(12) United States Patent
Regula

(10) Patent No.: US 6,283,963 B1
(45) Date of Patent: Sep. 4, 2001

(54) BIPOLAR ELECTROSURGICAL SCISSORS FOR FINE OR DELICATE SURGICAL DISSECTION

(75) Inventor: Donald W. Regula, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/167,869

(22) Filed: Oct. 7, 1998

Related U.S. Application Data
(60) Provisional application No. 60/062,661, filed on Oct. 8, 1997.

(51) Int. Cl.[7] .................................................. A61B 18/14
(52) U.S. Cl. .................................. 606/48; 606/50; 606/51
(58) Field of Search ............................ 606/45, 46, 48–52

(56) References Cited

U.S. PATENT DOCUMENTS

| | | | |
|---|---|---|---|
| 4,681,105 | * 7/1987 | Tritt | 606/52 |
| 5,324,289 | 6/1994 | Eggers . | |
| 5,330,471 | 7/1994 | Eggers . | |
| 5,352,222 | 10/1994 | Rydell . | |
| 5,484,436 | 1/1996 | Eggers et al. . | |
| 5,514,134 | 5/1996 | Rydell et al. . | |
| 5,540,685 | 7/1996 | Parins et al. . | |
| 5,700,261 | * 12/1997 | Brinkerhoff | 606/50 |
| 5,827,281 | * 10/1998 | Levin | 606/51 |

FOREIGN PATENT DOCUMENTS

| | | |
|---|---|---|
| 0 517 244 A1 | 12/1992 | (EP) . |
| 0 765 639 A1 | 9/1995 | (EP) . |
| 0 717 966 A1 | 12/1995 | (EP) . |
| 197710 | * 10/1977 | (SU) .................................. 606/48 |
| WO 96/27338 | 9/1996 | (WO) . |
| WO 96/33665 | 10/1996 | (WO) . |

OTHER PUBLICATIONS

Stevenson, "Combined Diathermy Forceps And Scissors", The Lancet, pp. 650–651, Oct. 24, 1959.*

* cited by examiner

*Primary Examiner*—Lee Cohen
(74) *Attorney, Agent, or Firm*—Scully, Scott, Murphy & Presser

(57) ABSTRACT

A bipolar electrosurgical scissors having a first cutting blade which has a first cutting portion, the first cutting portion having a corresponding first cutting edge; a second cutting blade which has a second cutting portion, the second cutting portion having a corresponding second cutting edge in cutting cooperation with the first cutting edge; and electrical insulation disposed on portions of the first and second cutting blades, the electrical insulation extending into the first and second cutting portions except for the corresponding cutting edges for preventing electrical conduction from the electrically insulated portions of the cutting blades. In a first embodiment of the bipolar electrosurgical scissors of the present invention, the electrical insulation extends into the first and second cutting blades such that ⅓ of their distal tip is uninsulated. In a second embodiment of the bipolar electrosurgical scissors of the present invention, the electrical insulation extends into the first and second cutting members such that they are entirely insulated except for their corresponding cutting edges.

18 Claims, 14 Drawing Sheets

Current Production

Thermocouples
Relative Position
(approximates)

TC1, L minus 3mm
TC2, 2/3 L
TC3, midpoint of L
TC4, O plus 3 mm
TC5, O minus 3 mm Extended Nylon Thermocouples
Relative Position
(approximates)

TC1, L minus 3 mm
TC2, midpoint of L
TC3, O plus 3 mm
TC4, O minus 3 mm

FIG. 5

Per the protocol

| T/C | Ambient log-25 cut35w/std | T-Ttis | Ambient log-26 cut35w/ext | T-Ttis | Ambient log-27 cut35w/std | T-Ttis | Ambient log-28 cut35w/ext | T-Ttis | Ambient log-29 cut35w/ext | T-Ttis | Ambient log-30 cut35w/ext | T-Ttis |
|---|---|---|---|---|---|---|---|---|---|---|---|---|
| 1 | 40 | 20 | 37 | 17 | 43 | 23 | 44 | 24 | 34 | 14 | 36 | 16 |
| 2 | 42 | 22 | 43 | 23 | 43 | 23 | 46 | 26 | 35 | 15 | 37 | 17 |
| 3 | 45 | 25 | 51 | 31 | 47 | 27 | 43 | 23 | 35 | 15 | 38 | 18 |
| 4 | 39 | 19 | 46 | 26 | 43 | 23 | 41 | 21 | 36 | 16 | 38 | 18 |
| 5 | 43 | 23 | 48 | 28 | 47 | 27 |   |   |   |   |   |   |

Experiment with warm tissue

| WarmTissue log-32 cut35w/std | T-Ttis | WarmTissue log-33 cut35w/ext | T-Ttis |
|---|---|---|---|
| 39 | 2 | 43 | 6 |
| 45 | 8 | 46 | 9 |
| 63 | 26 | 47 | 10 |
| 75 | 38 | 51 | 14 |
| 76 | 39 |   |   |

Repeat of protocol with warm tissue

| WarmTissue log-048 cut35w/ext | T-Ttis | WarmTissue log-050 cut35w/ext | T-Ttis | WarmTissue log-052 cut35w/ext | T-Ttis | WarmTissue log-49 cut35w/std | T-Ttis | WarmTissue log-53 cut35w/std | T-Ttis | WarmTissue log-051 cut35w/std | T-Ttis |
|---|---|---|---|---|---|---|---|---|---|---|---|
| 51 | 14 | 44 | 7 | 48 | 11 | 47 | 10 | 37 | 0 | 39 | 2 |
|   | 18 | 51 | 14 | 50 | 13 | 56 | 19 | 42 | 5 | 37 | 0 |
| 55 | 22 | 55 | 18 | 47 | 10 | 67 | 30 | 48 | 11 | 54 | 17 |
| 59 |   | 69 | 32 | 46 | 9 | 55 | 18 | 47 | 10 | 48 | 11 |
|   |   |   |   |   |   | 61 | 24 | 49 | 12 | 50 | 13 |

BIPOLAR ELECTROSURGICAL SCISSORS FOR FINE OR DELICATE SURGICAL DISSECTION

CROSS REFERENCE TO RELATED APPLICATIONS

This application is a conversion of U.S. Provisional Application Ser. No. 60/062,661, filed Oct. 8, 1997.

BACKGROUND OF THE INVENTION

1. Field of the Invention

The field of art to which this invention relates is surgical instruments, in particular, electrosurgical cutting and grasping instruments.

2. Description of the Related Art

Two techniques used extensively in both open and endoscopic surgery are (a) the controlling of bleeding using electrosurgical instrumentation and (b) the incision or severing of tissue or vessels. The control of bleeding during surgery accounts for a major portion of the time involved in surgery. In particular, bleeding that occurs when tissue is incised or severed can obscure the surgeon's vision, prolong the operation, and adversely effect the precision of cutting. Blood loss from surgical cutting may require blood infusion, thereby increasing the risk of harm to the patient.

Hemostatic electrosurgical techniques are known in the art for reducing bleeding from incised tissue prior to, during, and subsequent to incision. Electrosurgical cutting and coagulating instruments are used to perform such techniques. These instruments can be of a reusable type (which require cleaning and disinfecting or sterilizing before each use) or disposable (which are disposed of after a single use). Each type includes both monopolar and bipolar variations having at least one electrode. Radio frequency (RF) energy is conducted through this electrode to either a remote conductive body-plate (known as a grounding pad) in the case of monopolar instruments, or to a second, closely spaced conductive electrode in the case of bipolar instruments. In monopolar instruments electrical current travels from the electrode through the patient's body to the grounding pad. Bipolar instruments are typically connected to both poles of an electrosurgical generator, therefore current flow is typically limited to tissue adjacent to the working end of the bipolar instrument (where the two electrodes are located).

Standard shape and size scissors have evolved in the surgical arts which surgeons have become accustomed to. These standards have been incorporated into the electrosurgical scissors, not only because they have been tested by time and found to be very functional, but mainly because surgeons have become accustomed with their feel and use. Examples of some of these standards include the Mayo, Metzenbaum, and Tenotomy scissors. Each standard scissor is typically available in both curved and straight variations.

Recent research and post-market surgical use has indicated the need for variations of these standard shape and size electrosurgical scissors, preferably of the bipolar variety. Current standard shape and size electrosurgical scissors include: 4½" Tenotomy; 7", 9" and 11" Metzenbaum; and 6¾" Mayo styles. These scissors were developed to fit general scissor requirements for general, GYN and plastic surgical procedures. The technology has been well received, and evaluations of the scissors have expanded to the surgical specialties of otolaryngology, ENT, vascular, cardiovascular, urology, thoracic, neurology and pediatric surgery. This expansion into additional surgical specialties has opened the need for additional variations which will more closely replicate the existing style or size of the standard surgical scissors in current use. Research indicates that additional scissor variations are needed to take advantage of current trends in procedural usage. Some proposed scissor styles, ranked in descending order for proposed greatest use, include: 7", 9" fine-tip Metzenbaum, 7" Tenotomy, 9" Mayo, 11" fine-tip Metzenbaum and a 5½" fine-tip Metzenbaum. The addition of a fine-tip Metzenbaum (5½", 7", 9", 11"), a 7" Tenotomy and a 9" Mayo allows for expansion into additional surgical specialties or specific procedures.

In addition to these variations, it is also desired to modify the amount or length of electrical insulation distally toward the scissor tips. This would increase the amount of electrical insulation on the blades, therefore, decreasing the zone where current or thermal effect could be delivered. This would make the scissor easier to use and would allow surgeons to work closer to delicate structures with increased comfort and control. This enhancement has particular benefits in procedures involving close work to sensitive structures such as otorhinolaryngology or plastic procedures (e.g., tonsillectomies, facelifts, blepharoplasties, tram flaps, free flaps, laryngectomies, thyroidectomies), general procedures (e.g., carotidectomies, carotid enarterectomy, radical neck dissections for CA), and CV/vascular/thoracic procedures (e.g., CABG IMA harvest and/or saphenous vein, mitral or aortic valve replacement, congenital defect repairs, femoral popliteal or tibular bypass, abdominal aortic aneurysm, lung biopsy, thoracotomy, wedge resection).

The configuration of the insulating coating on the blades of the bipolar scissors has been a design criterion since the conception of bipolar scissors. To understand its relevance, a brief discussion of how the scissors function will be helpful.

With bipolar scissors, a first blade is the first active electrode and is disposed at the distal end of a first handle. The second blade is the second electrode of opposite polarity and is disposed at the distal end of a second handle. One of the first and second blades is insulated from the other blade by a first insulating coating, preferably aluminum oxide, on the shearing surface, i.e., the cutting edge of the blade and by a second insulating coating, also preferably aluminum oxide, on the pivot screw. A third insulating coating is disposed on the handles, including the area around the pivot screw and on a "portion" of the non-shearing, outside surfaces of the blades. The electrical insulation provides electrical insulation to prevent passage of electrical RF current, so that these insulated areas can contact non-targeted patient tissue, or be touched by the surgeon or surgical assistants. When the scissors are activated, the path of RF current is through the targeted tissue that is in contact with the uninsulated portions of the blades. The surgeon can control the amount of tissue that is exposed to RF energy and the portion of an uninsulated blade surface exposed to the tissue.

In standard electrosurgical scissors, the configuration of the electrical insulation was such that the exposed or uninsulated surface of both blades was defined by the length of blade that was ground to produce the cutting edge. This would allow the surgeon to utilize the full range of that "cutting-area" to effect coagulation of tissue. While the standard electrosurgical scissors of the prior art have their advantages, in surgical procedures performed in confined areas or in delicate anatomy, they can lead to cauterization of unintended tissue.

Accordingly, there is a need in the art for an improved electrosurgical instrument designed for procedures involving close work to sensitive structures and which remain in a standard scissor shape and size.

SUMMARY OF THE INVENTION

Therefore, it is an object of the present invention to provide a bipolar electrosurgical scissor for fine or delicate surgical dissection.

It is yet another object of the present invention to provide a bipolar electrosurgical scissor for fine or delicate surgical dissection in which the possibility that unintended tissue is accidentally cauterized is minimized.

It is still yet another object of the present invention to provide a bipolar electrosurgical scissor for fine or delicate surgical dissection in which the above objectives are met without decreasing the cutting length of the scissor.

Accordingly, a bipolar electrosurgical scissor is provided. The bipolar scissors comprises a first cutting blade having a first cutting portion, the first cutting portion having a corresponding first cutting edge; a second cutting blade having a second cutting portion, the second cutting portion having a corresponding second cutting edge in cutting cooperation with the first cutting edge; and electrical insulation disposed on portions of the first and second cutting blades, the electrical insulation extending into the first and second cutting portions except for the corresponding cutting edges for preventing electrical conduction from the electrically insulated portions of the cutting blades.

In a first embodiment of the bipolar electrosurgical scissors of the present invention, the electrical insulation extends into the first and second cutting blades such that ⅓ of their distal tip is uninsulated.

In a second embodiment of the bipolar electrosurgical scissors of the present invention, the electrical insulation extends into the first and second cutting members such that they are entirely insulated except for their corresponding cutting edges.

BRIEF DESCRIPTION OF THE DRAWINGS

These and other features, and advantages of the instruments and methods of the present invention will become better understood with regard to the following description and accompanying drawings where:

FIG. 2 is for a 7" Metzenbaum having a standard electrical insulation coating, and FIG. 3 is for a 7" Metzenbaum having an extended electrical insulation coating;

FIGS. 5 and 6 illustrate the pin-point coagulation cool down time at 35 watts for both a 7 inch Metzenbaum having a standard electrical insulation coating and a 7 inch Metzenbaum having an extended electrical insulation coating;

DETAILED DESCRIPTION OF THE PREFERRED EMBODIMENT

It has been recognized that only the distal third of the blade is utilized for most dissection and in particular for delicate dissection. However, surgeons also indicate that they utilize the full cutting edges of the blades in many procedures. Therefore, an effective bipolar scissors for the above mentioned delicate procedures is provided to be useful for a broad spectrum of surgical needs.

It has also been recognized that certain plastic and cardiovascular procedures in which only the distal third or less of the cutting edge is used for fine or delicate dissections, a finer tip design would be helpful. Since the entire blade is not needed for these procedures, in the present invention, the electrical insulation is moved distally to insulate more of the blade. Exposing less of the blade would allow surgeons to target a smaller area of tissue for coagulation and facilitate the procedure.

In a first embodiment of the electrosurgical bipolar scissors of the present invention, the electrical insulation coating is extended such that ⅓ of the distal cutting portion is left exposed. In a second embodiment, the entire cutting portion of the scissors are insulated. The electrical insulation coating is preferably a thermoplastic, such as nylon, and most preferably nylon 11 because of its low moisture retention and absorption properties. This is particularly important if the instrument is reusable and undergoes repeated sterilization.

Testing has been conducted on bipolar scissors with the electrical insulation extended towards the distal tip to measure the temperature at various points along the outer surface of the blade and on the outer surface of the electrical insulation near the electrical insulation/metal junction. The measurements estimate blade surface temperature reached during a surgical procedure, the time required for the blade surface to cool down to ambient temperature, and compare the surface temperatures of the blade and electrical insulation.

Figure 1A:
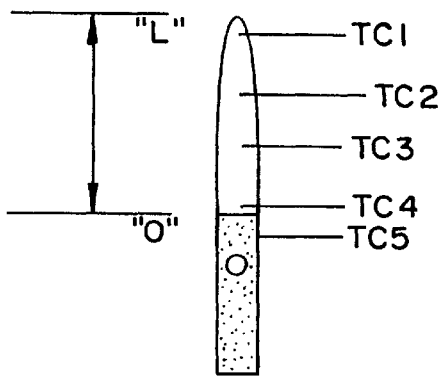
FIGS. 1A and 1B illustrate thermocouple locations on the distal end of a standard bipolar scissors and one in which the electrical insulation is extended distally, respectively.
Figure 1B:
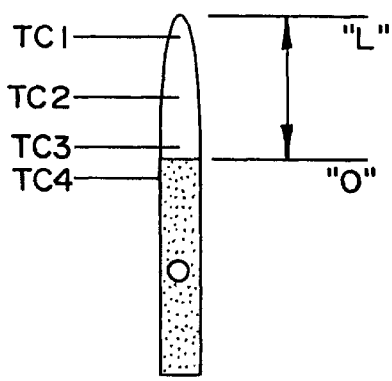
Figure 2:
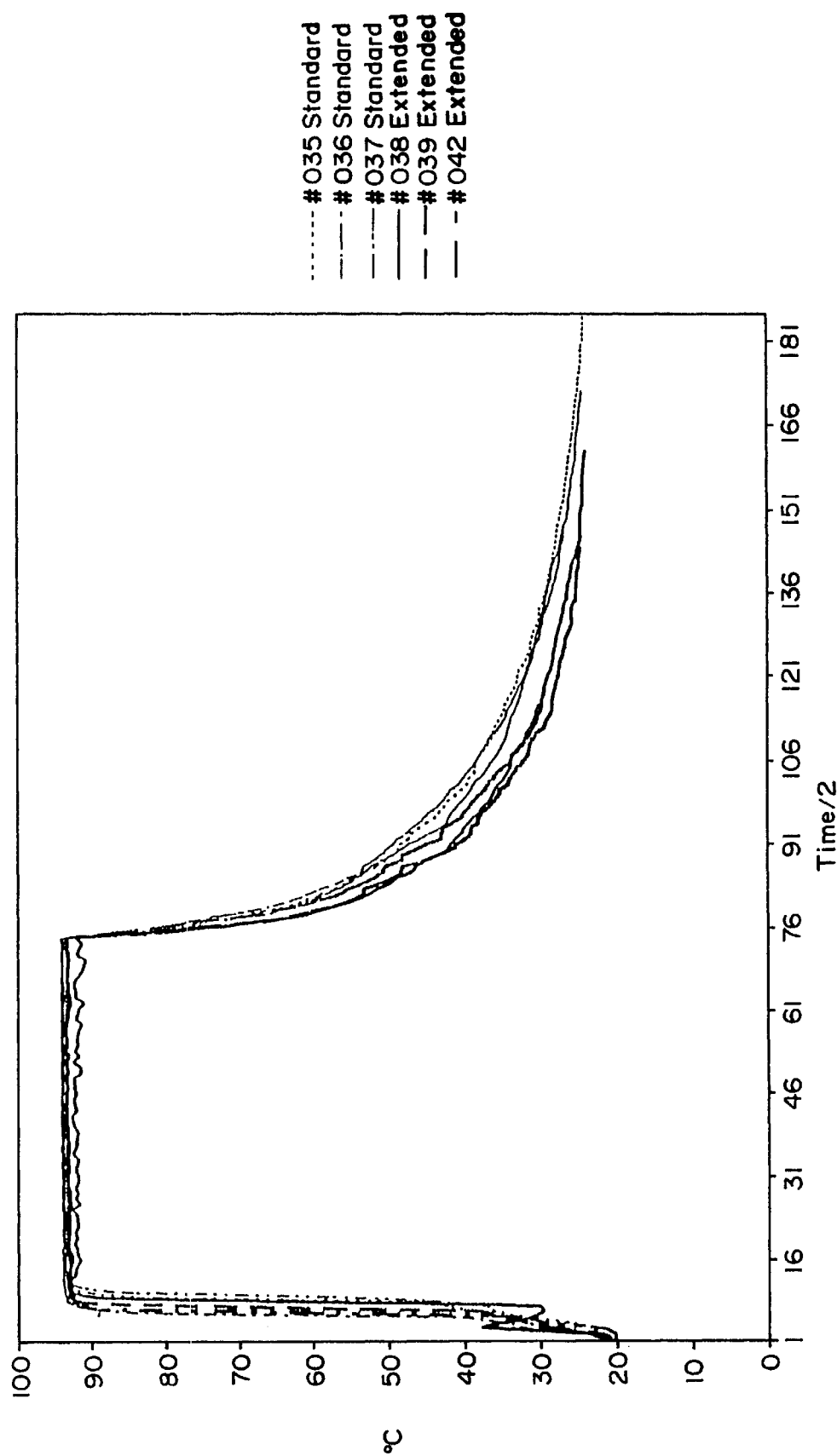
FIGS. 2 and 3 illustrate graphs showing blade surface thermocouple response.
Figure 3:
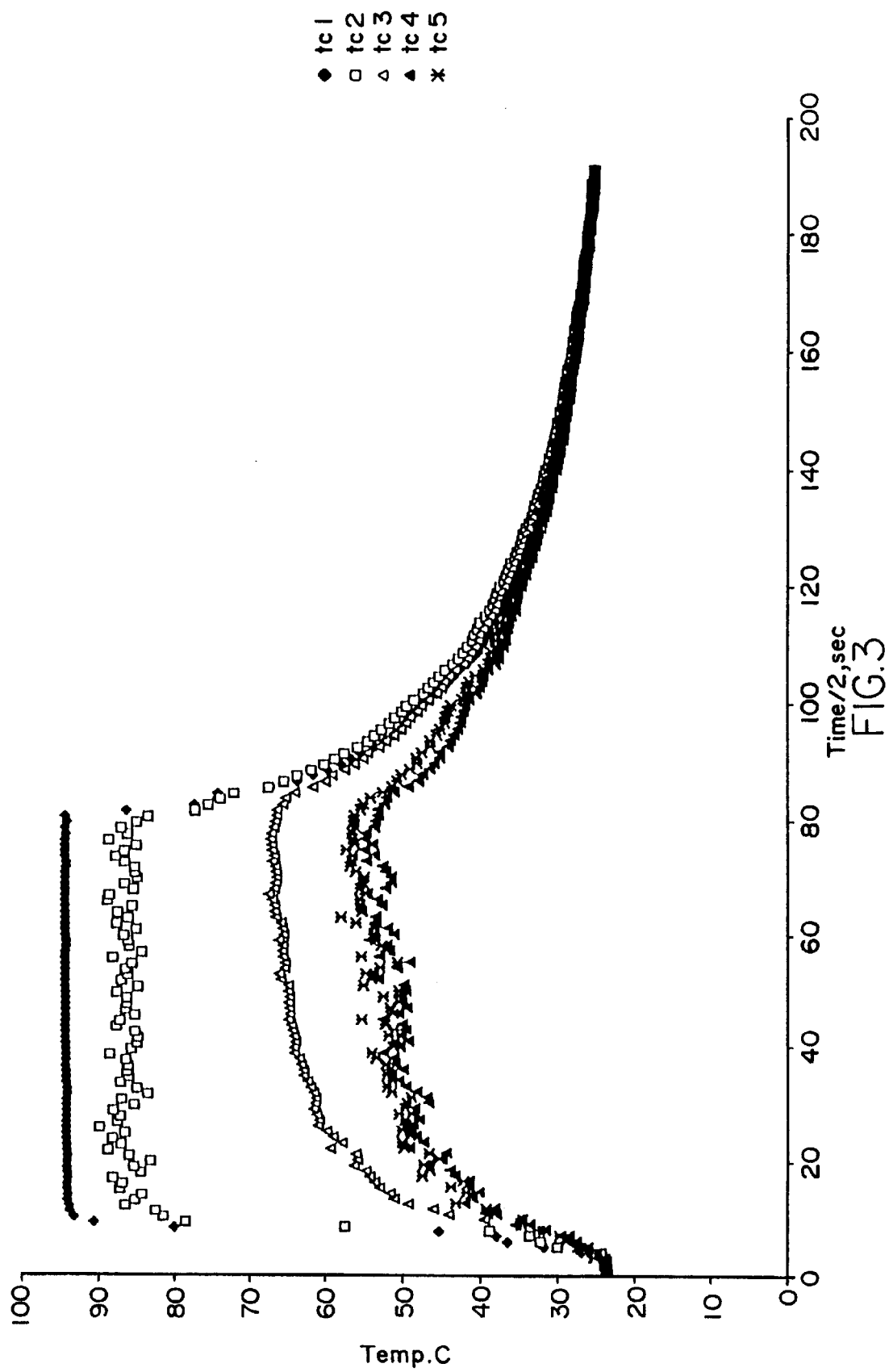
Figure 4:
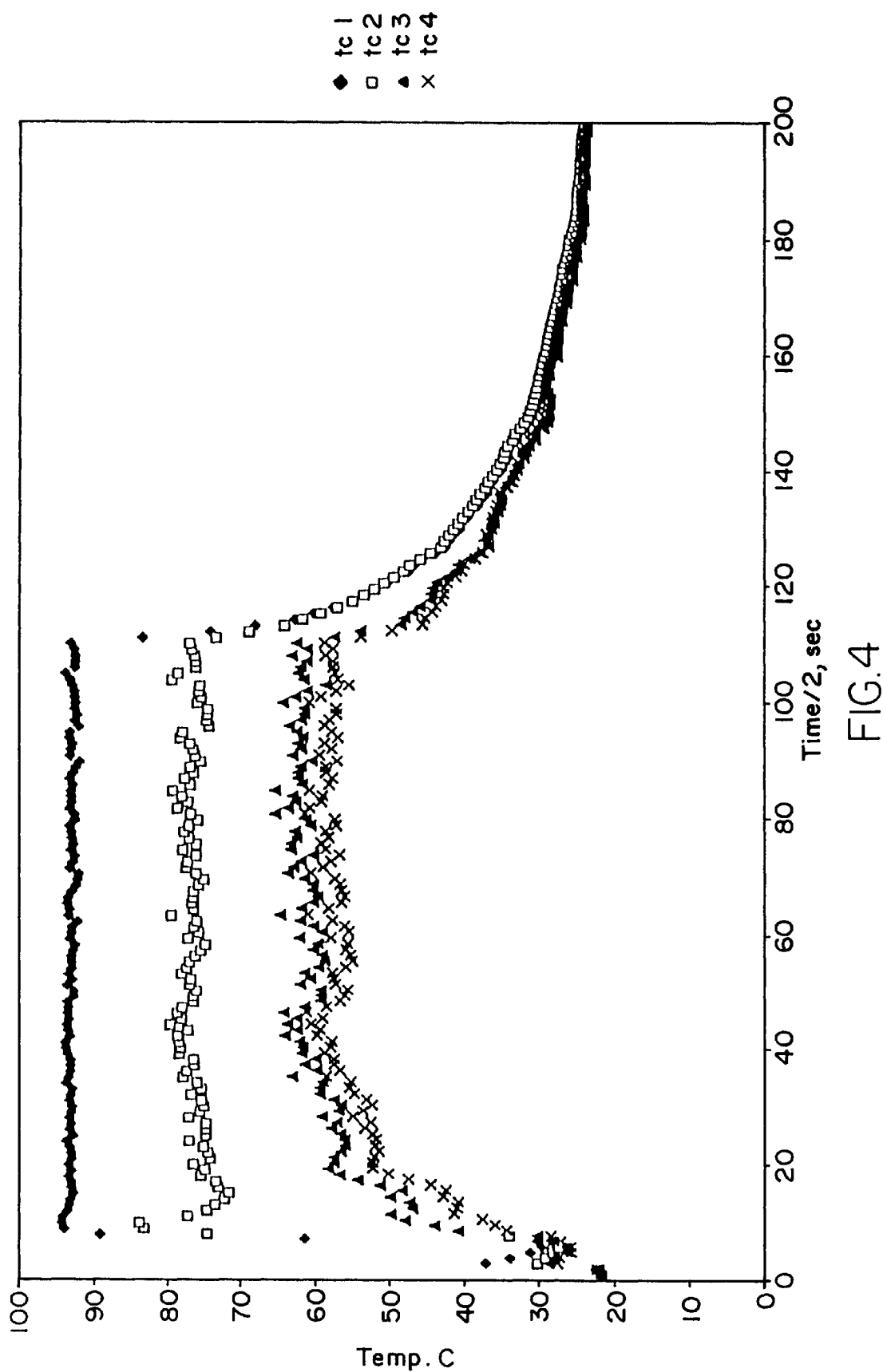
FIG. 4 illustrates a table which summarizes the tissue cutting experiments.
Figure 6:
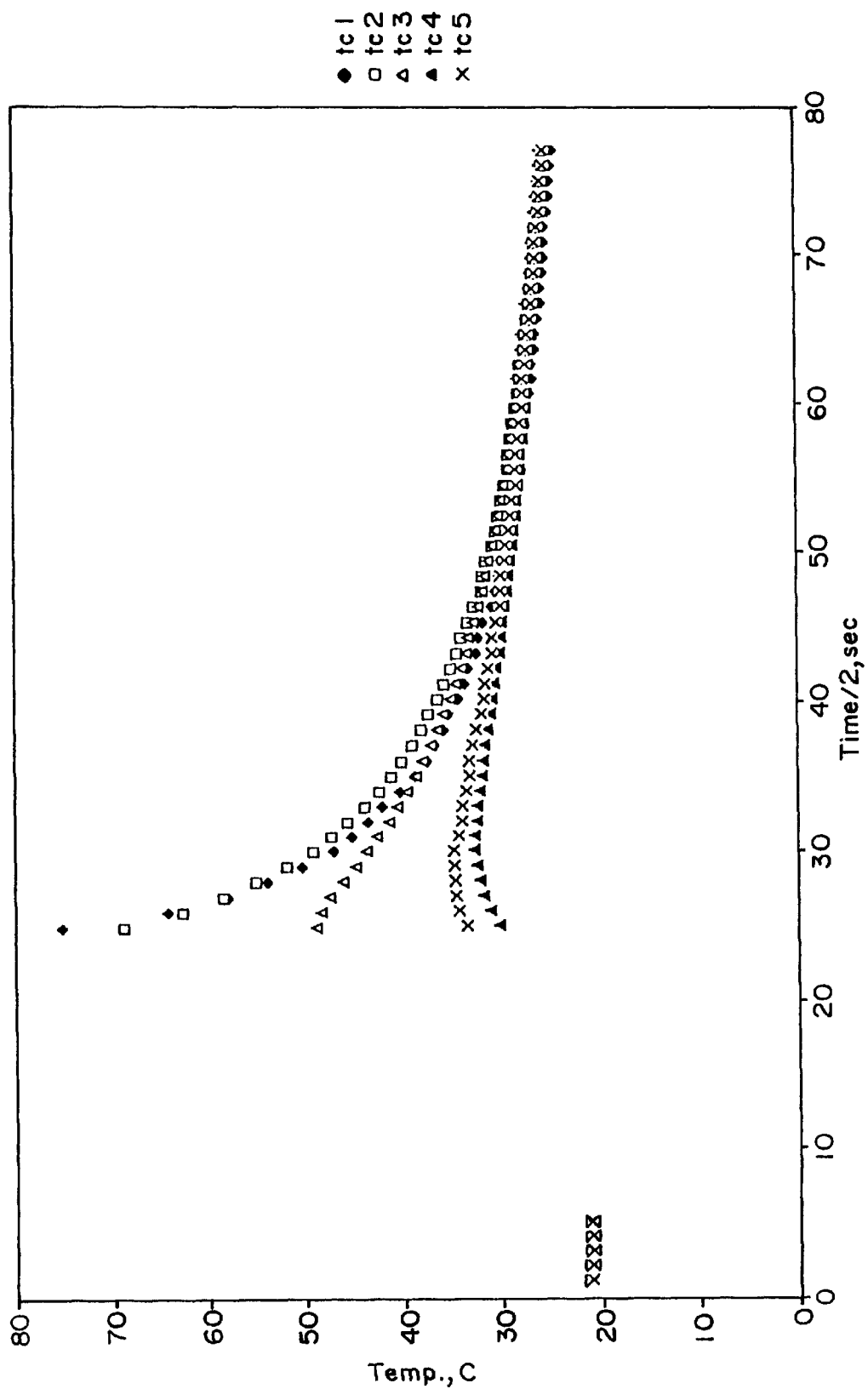
Figure 7:
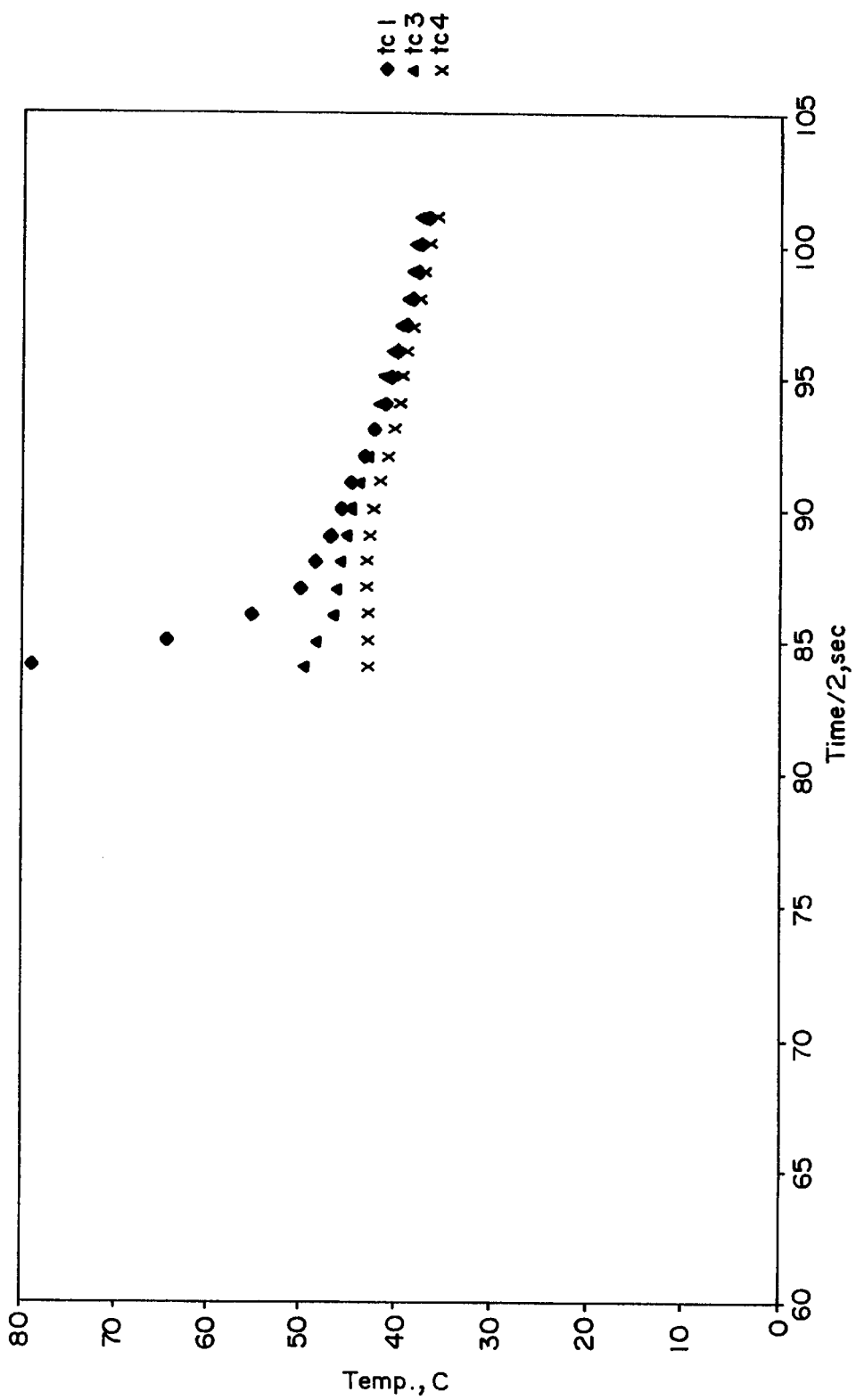
FIGS. 7 and 8 illustrate the pin-point coagulation cool down time at 70 watts for both a 7 inch Metzenbaum having a standard electrical insulation coating and a 7 inch Metzenbaum having an extended electrical insulation coating.
Figure 8:
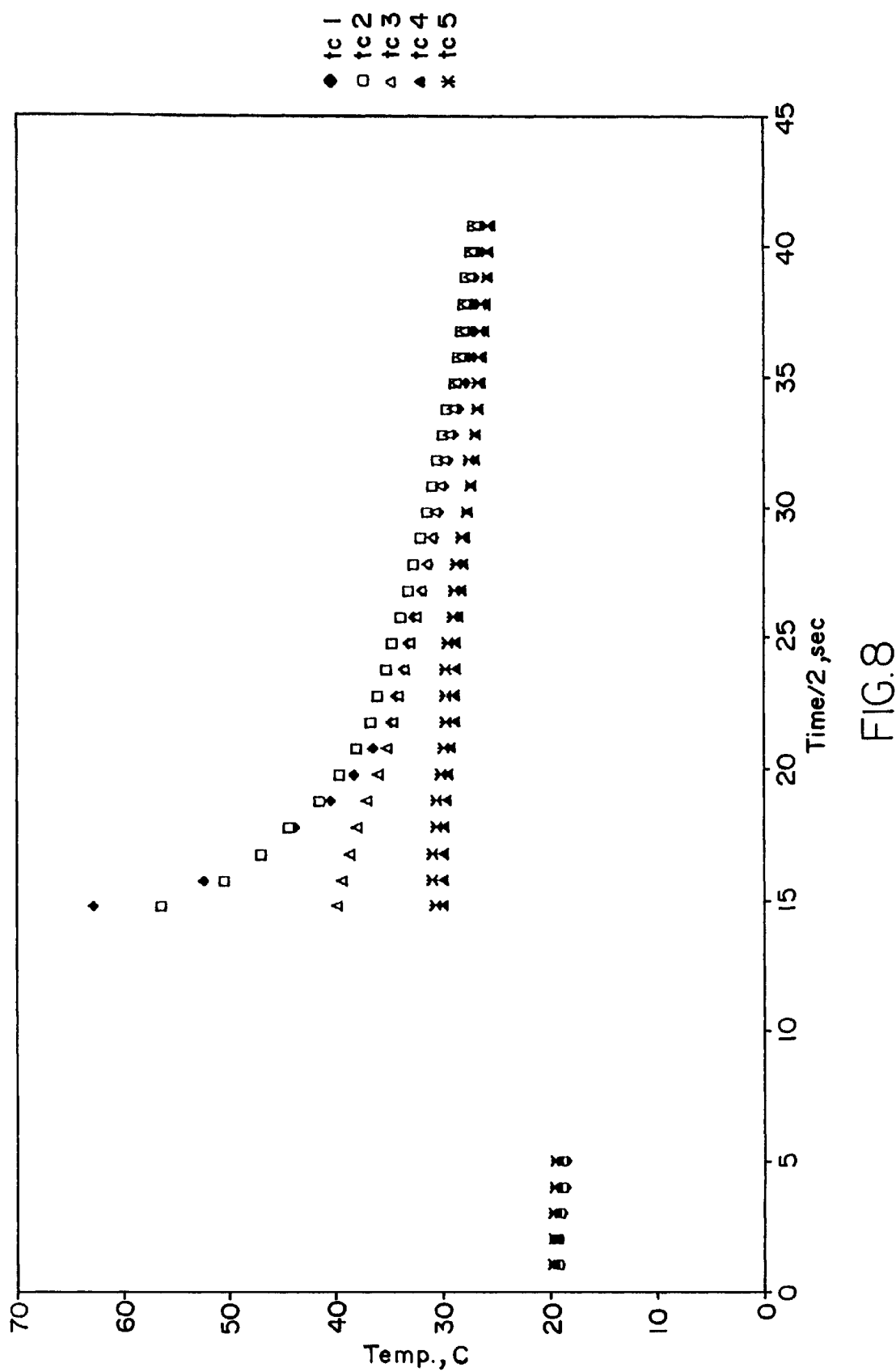

FIGS. 1A and 1B show the location of the thermocouples for a standard bipolar scissors and for a bipolar scissors with the extended electrical insulation, respectively. To determine that the thermocouples were functioning properly, a constant temperature bath and calibrated temperature recorder were used. The tips of the scissors (designated as location "TC1") were immersed in the bath, and the temperatures at the different locations (TC2–TC5) were recorded during heat up and cool down.

Porcine abattoir tissue was used to simulate a surgical procedure. Each cycle or "procedure" consisted of 200 cuts of the tissue at a bipolar generator setting of 35 watts. This cycle has been used in numerous studies to simulate reuse in surgery. Two tissue temperatures were used—ambient room air temperature (19° C. to 20° C.) and 37° C. The temperatures at the different locations were recorded during the 200 cut cycle to record the approximate maximum steady state temperature. The scissors were then allowed to cool in air, and the temperatures at the different locations were recorded.

An experiment was conducted which used a continuous "painting technique" to simulate pin-point coagulation of tissue. This was conducted at generator settings of 35 and 70 watts. Temperatures were recorded at the end of the 200 second cycles, and during cool down in air at ambient temperature.

The results of the testing showed that for the bath tested scissors, the tip of the blade cooled down from about 95° C. to about 37° C. at an average rate of about 1.4 to 1.9° C./second in about 60 seconds. In the tissue cutting study, the highest temperature measurement recorded was near the point of tissue contact and was less than 70° C. The cool down time after a 200 cut cycle from 70° C. to ambient is less than 60 seconds. In some situations, an extended electrical insulation affords a 5° C. to 10° C. temperature reduction when compared to the similarly sized and shaped standard bipolar scissor; although the primary function of the electrical insulation is to electrically insulate. With the "painting technique" the cool down time after a 200 second cycle from the maximum temperature recorded at the tip (location "TC1") of about 70° C. to ambient is less than 60 seconds. Within experimental repeatability for these simulated real life surgical procedures the thermal behavior of the extended and standard configurations are about equal. These test results are summarized in graphical and tabular form in FIGS. 2–8.

Figure 9:
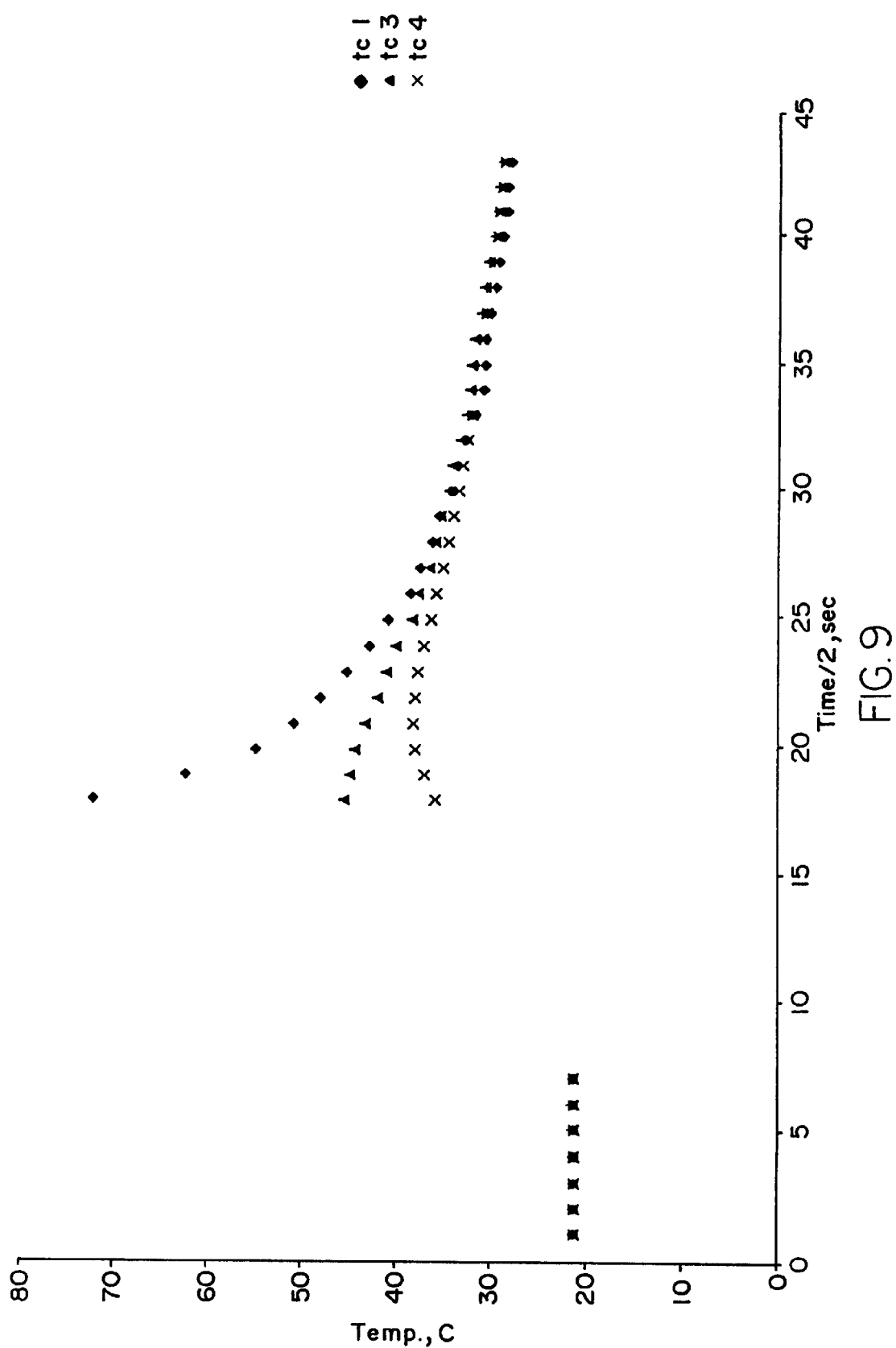
FIG. 9 illustrates a 7 inch Tenotomy scissors having the extended electrical insulation of the present invention.
Figure 10:
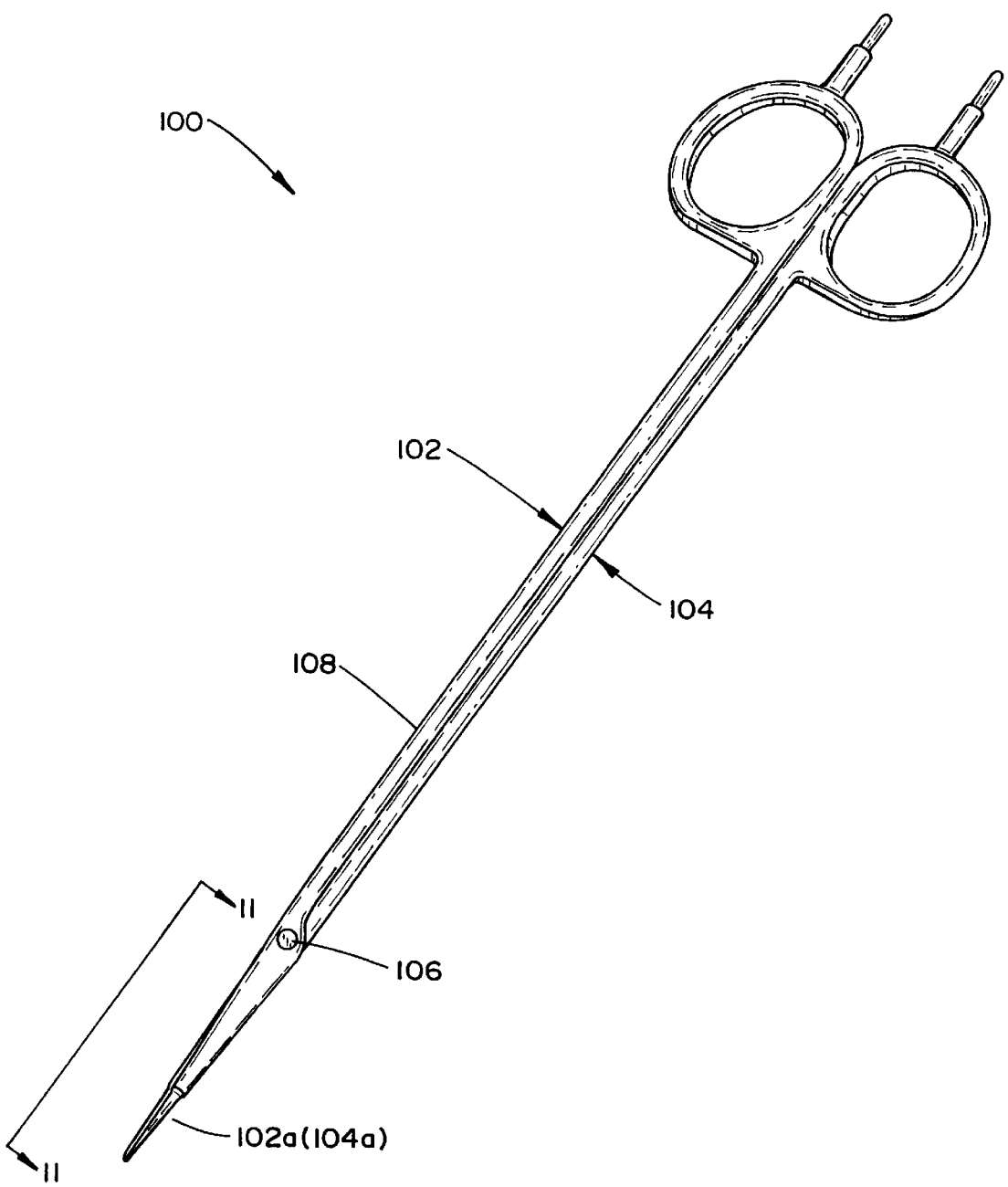
FIG. 10 illustrates an enlarged view of the distal end of the 7 inch Tenotomy scissors of FIG. 10 as viewed along line 11—11 in FIG. 10.

Referring now to FIG. 9, there is illustrated a 7 inch Tenotomy bipolar scissor of the present invention generally referred to by reference numeral 100. The Tenotomy scissors 100 have a first handle 102 and a second handle 104. At the distal end of each handle is a cutting blade 102a, 104a. The handles 102, 104 pivot about a pivot screw 106 such that the blades 102a, 104a cooperate with each other to form a scissor. An electrically insulating coating 108, preferably a thermoplastic such as nylon 11, as discussed above, extends distally towards the tip region 110 of the blades 102a, 104a to provide a scissor tip 110 which decreases the zone where current or thermal effect could be delivered. This allows a surgeon to work closer to delicate structures with increased comfort and control. Insulating coatings are also present around the pivot screw 106 and on a shearing surface of one of the blades to electrically isolate one handle from the other.

Figures 12A, 12B, 12C:
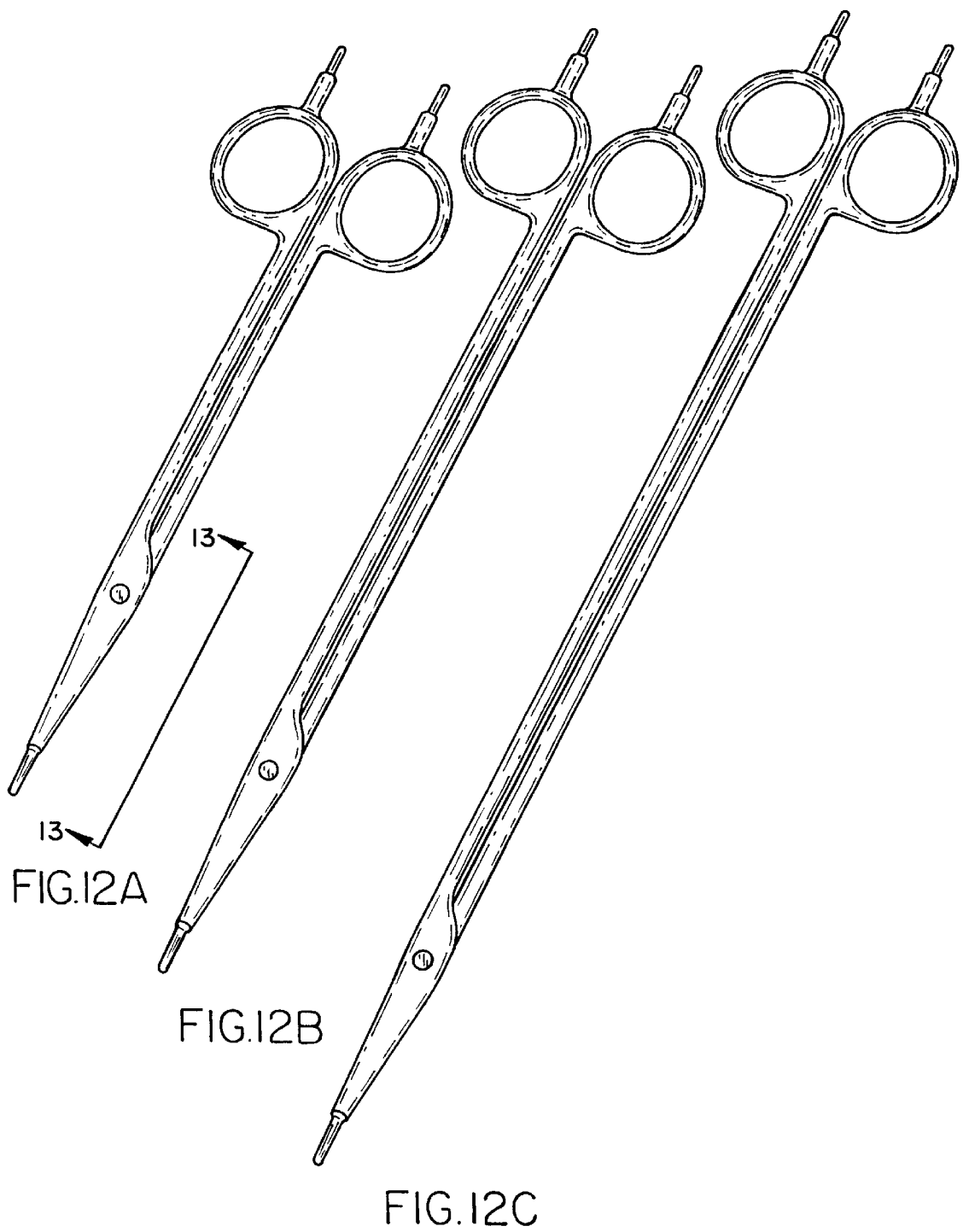
FIG. 12 illustrates an enlarged view of the distal end of the Metzenbaum scissors of FIG. 11A as viewed along line 12—12 in FIG. 11A.

Each cutting blade 102a, 104a has a corresponding cutting edge 102b, 104b, shown in FIG. 12, which is generally ground into the cutting portions of the cutting blades 102a, 104a. The electrical insulation 108 extends into the cutting portions of the cutting blades 102a, 104a thereby electrically insulating a portion of the blades 102a, 104a except for their corresponding cutting edge 102b, 104b.

Figure 13:
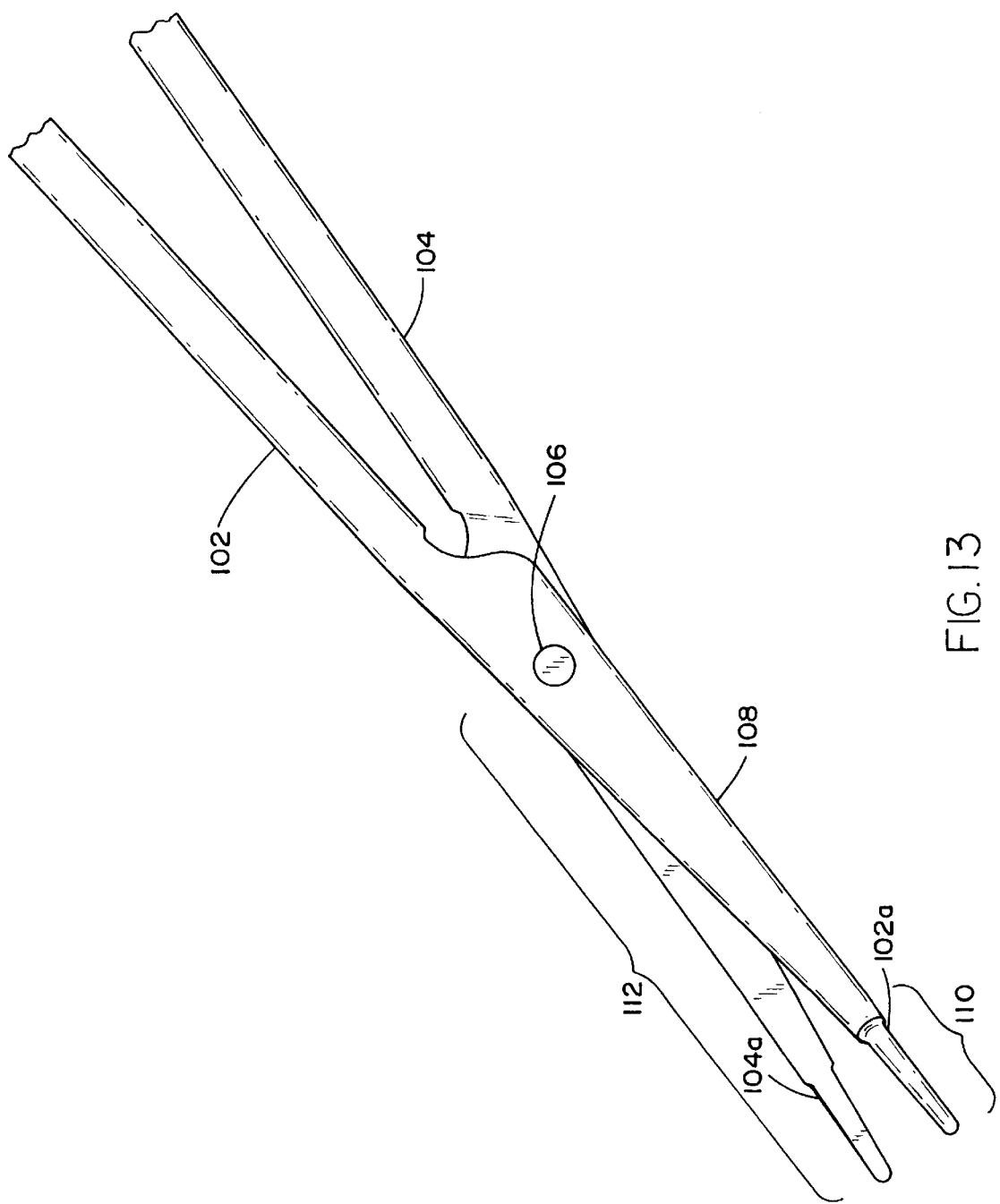
FIG. 13A illustrates a plan view of the distal end of a fine tip bipolar scissors of the present invention in which the standard tip profile is shown as a dashed line.
FIG. 13B illustrates a side view of the distal end of a fine tip bipolar scissors of the present invention in which the standard tip profile is shown as a dashed line.
FIG. 13C illustrates a sectional view of the fine tip bipolar scissors of FIG. 13A as taken along line 13C—13C and in which the standard tip profile is shown as a dashed line.

Preferably, the tip 110 of the electrosurgical bipolar scissors 100 of the present invention also differs from the prior art scissors in that it is of finer size and shape, which also facilitates work with delicate structures. FIGS. 13A, 13B, and 13C show a preferred fine tip profile of a scissor tip in comparison to a standard tip shown in dashed lines.

Figure 11:
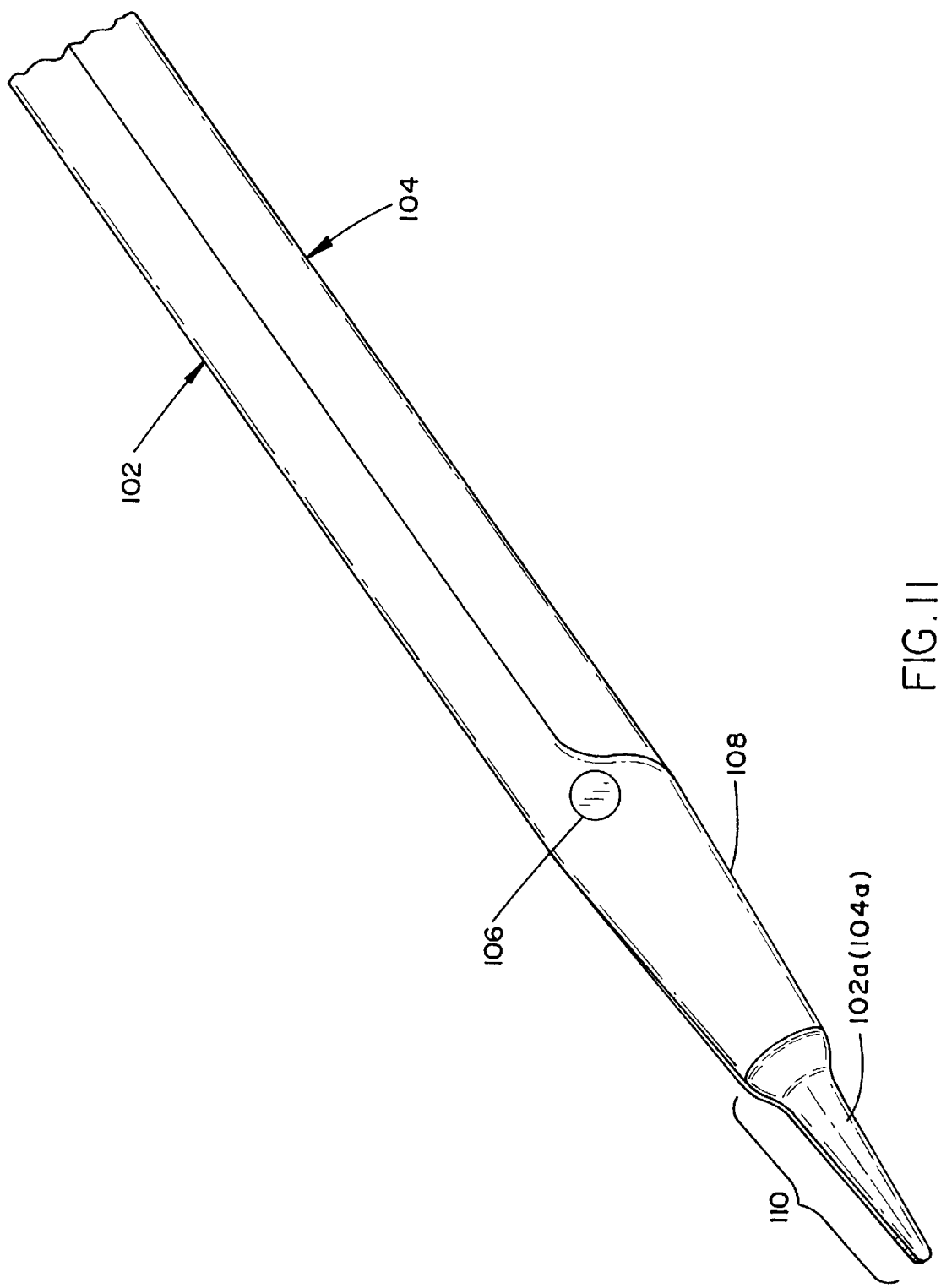
FIGS. 11A, 11E, and 11C illustrate 7, 9, and 11 inch fine tip Metzenbaum scissors, respectively, each scissor having the extended electrical insulation of the present invention.

The present invention has been described with regard to a Tenotomy scissor, however, it is understood by someone skilled in the art that any standard scissor, such as a Mayo or Metzenbaum, can utilized without departing from the scope and spirit of the invention. Examples of such scissor types are shown in FIGS. 11A, 11B, and 11C in which different size Metzenbaum scissors are illustrated having a fine tip and an insulating coating extended distally. FIG. 12 illustrates an enlarged view of the tip of FIG. 11A. It should be pointed out that the blade length 112 is much greater in size than the unexposed tip portion 110. In the preferred embodiment, the unexposed tip portion 110 of the cutting blades 102a, 104a is approximately ⅓ the overall length of the cutting portion of the cutting blades 102a, 104a, i.e., the cutting edges 102b, 104b. Therefore, a surgeon can both utilize the large blade length for cutting tissue and the fine tip with distally extended electrical insulation coating when working with delicate structures.

Figure 14A:
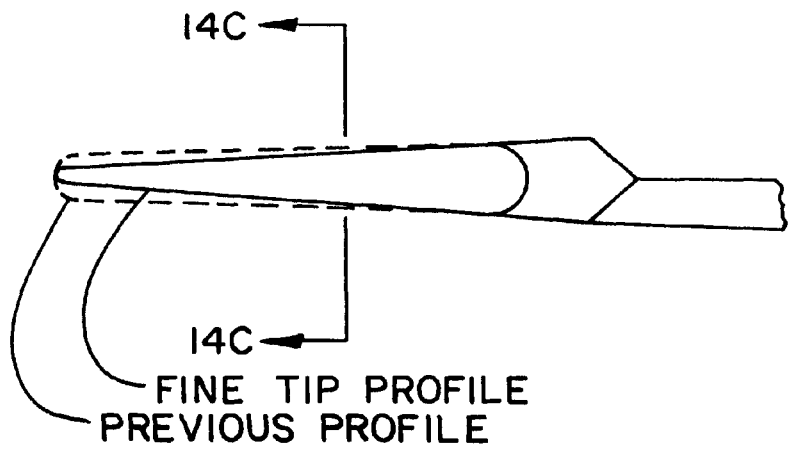
FIG. 14 illustrates a plan view of a bipolar electrosurgical scissors of the present invention according to a second embodiment in which the cutting members are entirely insulated except for the cutting edges.
Figure 14B:
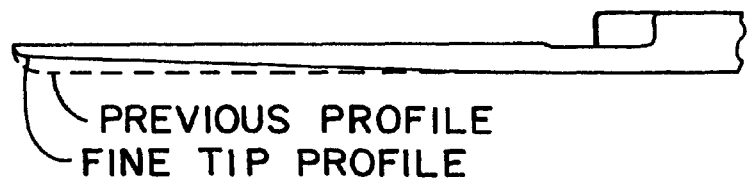
Figure 14C:

Referring now to FIG. 14, there is illustrated a second embodiment of the bipolar electrosurgical scissors of the present invention in which the electrical insulation covers the entire cutting blades 102a, 104a except for the cutting edges 102b, 104b. The second embodiment of the bipolar electrosurgical scissors in which like reference numeral designate like features from the first embodiment, is generally referred to by reference numeral 200.

In the bipolar scissors of the prior art, the electrical insulation ends along a plane perpendicular to the point on the cutting member, or blade, where the ground cutting edge begins. In the second embodiment of the bipolar scissors of the present invention, only the ground cutting edges 102b, 104b of each cutting blade 102a, 104a is exposed, the remainder of the cutting blades 102a, 104a being insulated with the electrical insulation 108. The loss of the non-insulated surfaces available for passage of current and cauterization is compensated by the increased current density concentrated at the cutting edges of the fully insulated blades.

Of course, the variation in the tip size and scissor type as discussed above with regard to the first embodiment of the electrosurgical bipolar scissors of the present invention is equally applicable to the second embodiment.

Alternatively, the length of the cutting edge can also be varied by removing the ground edge and covering their surface with electrical insulation to further restrict and concentrate the current density at the cutting edges.

From the foregoing, it becomes readily apparent to one skilled in the art that the novel bipolar scissors offers improved comfort and control when performing procedures which necessitate working closely to delicate structures and which also offers the versatility of being able to perform large dissections, all of which renders the instrument much more effective in certain surgical procedures.

While there have been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

Having thus described our invention, what we claim as new, and desire to secure by Letters Patent is:

1. A bipolar electrosurgical scissors comprising:
a first cutting blade having a first cutting portion, the first cutting portion having a corresponding first cutting edge;
a second cutting blade having a second cutting portion, the second cutting portion having a corresponding second cutting edge in cutting cooperation with the first cutting edge; and
electrical insulation disposed on portions of the first and second cutting blades, the electrical insulation extending into the first and second cutting portions except for the corresponding cutting edges for preventing electrical conduction from the electrically insulated portions of the cutting blades;
wherein the electrical insulation extends into the first and second cutting blades such that ⅓ of a distal tip of the first and second cutting blades are uninsulated.

2. The bipolar electrosurgical scissors as claimed in claim 1, wherein the electrical insulation extends into the first and second cutting blades such that they are entirely insulated except for their corresponding cutting edges.

3. The bipolar electrosurgical scissors as claimed in claim 1, wherein the electrical insulation is a thermoplastic.

4. The bipolar electrosurgical scissors as claimed in claim 4, wherein the thermoplastic is nylon 11.

5. The bipolar electrosurgical scissors as claimed in claim 1, wherein the scissors in a Tenotomy scissor.

6. The bipolar electrosurgical scissors as claimed in claim 6, wherein the Tenotomy scissor has a fine tip for fine or delicate surgical dissection.

7. The bipolar electrosurgical scissors as claimed in claim 1, wherein the scissors is a Metzenbaum scissor.

8. The bipolar electrosurgical scissors as claimed in claim 8, wherein the Metzenbaum scissor has a fine tip for fine or delicate surgical dissection.

9. The bipolar electrosurgical scissors as claimed in claim 1, wherein the scissors is a Mayo scissor.

10. The bipolar electrosurgical scissors as claimed in claim 10, wherein the Mayo scissor has a fine tip for fine or delicate surgical dissection.

11. The bipolar electrosurgical scissors comprising:
a fine tip for fine or delicate surgical dissection, the fine tip comprising a first cutting blade having a first cutting portion, the first cutting portion having a corresponding first cutting edge and a second cutting blade having a second cutting portion, the second cutting portion having a corresponding second cutting edge in cutting cooperation with the first cutting edge; and
electrical insulation disposed on portions of the first and second cutting blades, the electrical insulation extending into the first and second cutting portions except for the corresponding cutting edges for preventing electrical conduction from the electrically insulated portions of the cutting blades.

12. The bipolar electrosurgical scissors as claimed in claim 11, wherein the electrical insulation extends into the first and second cutting blades such that ⅓ of a distal portion of the fine tip is uninsulated.

13. The bipolar electrosurgical scissors as claimed in claim 11, wherein the electrical insulation extends into the first and second cutting blades such that they are entirely insulated except for their corresponding cutting edges.

14. The bipolar electrosurgical scissors as claimed in claim 11, wherein the electrical insulation is a thermoplastic.

15. The bipolar electrosurgical scissors as claimed in claim 14, wherein the thermoplastic is nylon 11.

16. The bipolar electrosurgical scissors as claimed in claim 11, wherein the scissors is a Tenotomy scissor.

17. The bipolar electrosurgical scissors as claimed in claim 11, wherein the scissors is a Metzenbaum scissor.

18. The bipolar electrosurgical scissors as claimed in claim 11, wherein the scissors is a Mayo scissor.

* * * * *